US010551282B2

(12) United States Patent
Li et al.

(10) Patent No.: US 10,551,282 B2
(45) Date of Patent: Feb. 4, 2020

(54) APPARATUS AND METHOD FOR TESTING PERFORMANCE OF AN ELECTROSURGICAL TOOL

(71) Applicant: City University of Hong Kong, Kowloon (HK)

(72) Inventors: Kwok Yan Li, Kowloon (HK); Po Wan Shum, New Territories (HK); Zhifeng Zhou, Ma On Shan (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 194 days.

(21) Appl. No.: 15/430,676

(22) Filed: Feb. 13, 2017

(65) Prior Publication Data

US 2018/0231436 A1    Aug. 16, 2018

(51) Int. Cl.
G01M 99/00    (2011.01)
A61B 17/00    (2006.01)
A61B 18/00    (2006.01)

(52) U.S. Cl.
CPC . *G01M 99/008* (2013.01); *A61B 2017/00725* (2013.01); *A61B 2018/00601* (2013.01)

(58) Field of Classification Search
None
See application file for complete search history.

(56) References Cited

U.S. PATENT DOCUMENTS

| 9,539,433 | B1 * | 1/2017 | Wirbisky | A61N 1/38 |
| 10,016,603 | B2 * | 7/2018 | Sachs | A61N 1/36003 |
| 2004/0069488 | A1 * | 4/2004 | Chaplin | E21B 47/18 166/254.2 |
| 2007/0239224 | A1 * | 10/2007 | Bennett | A61N 1/0524 607/41 |
| 2007/0260288 | A1 * | 11/2007 | Gross | A61F 2/0045 607/41 |
| 2008/0132969 | A1 * | 6/2008 | Bennett | A61N 1/0558 607/41 |
| 2010/0209767 | A1 * | 8/2010 | Kasamatsu | H01M 6/50 429/178 |
| 2013/0338730 | A1 * | 12/2013 | Shiroff | A61N 1/0558 607/48 |
| 2015/0367136 | A1 * | 12/2015 | Rondoni | A61N 1/37217 607/42 |

(Continued)

FOREIGN PATENT DOCUMENTS

| CN | 103529378 A | 1/2014 |
| CN | 104127234 A | 11/2014 |

*Primary Examiner* — Natalie Huls
*Assistant Examiner* — Mohammed E Keramet-Amircolai
(74) *Attorney, Agent, or Firm* — Renner Kenner Greive Bobak Taylor & Weber

(57) ABSTRACT

An apparatus and a method for testing performance of an electrosurgical tool include a frame, a clamp module coupled to the frame and configured to retain a test material in a selected orientation, and a tool module coupled to the frame and configured to grip an electrosurgical tool. The apparatus is configured to: (a) allow a user to perform a controllable cut to evaluate a cutting performance of the electrosurgical tool based on a resistance force between the electrosurgical tool and the test material as the electrosurgical tool performs the controllable cut; and (b) evaluate a non-stickness of the electrosurgical tool after the electrosurgical tool performs the controllable cut.

22 Claims, 6 Drawing Sheets

(56) References Cited

U.S. PATENT DOCUMENTS

2016/0067476 A1\* 3/2016 Rawat .................. A61N 1/0551
　　　　　　　　　　　　　　　　　　　　606/129
2016/0076966 A1\* 3/2016 Khulief .................. G01M 7/06
　　　　　　　　　　　　　　　　　　　　73/663

\* cited by examiner

APPARATUS AND METHOD FOR TESTING PERFORMANCE OF AN ELECTROSURGICAL TOOL

TECHNICAL FIELD

The present disclosure relates to an apparatus for testing the performance an electrosurgical tool and a method of testing the performance of an electrosurgical tool. In particular, the present disclosure relates to an apparatus for testing the performance of an electrosurgical blade or cutter and a method of testing the performance of an electrosurgical blade or cutter.

BACKGROUND

Surgery and surgical techniques continue to evolve with advent and adoption of new medical technologies. Electrosurgery is a commonly used surgical technique in modern surgery. Electrosurgery is the application of high frequency, alternating polarity electrical current to biological tissue as a mechanism to cut, coagulate, desiccate or fulgurate tissue within a human body. Electrosurgery, in some instances, can be used instead of traditional surgery that uses scalpels, pliers and other surgical equipment. In a typical application, electrical current is applied to a preselected tissue or preselected surgical site using an electrosurgical instrument such as an electrosurgical blade.

An electrosurgical blade is a handheld instrument that includes an electrode. The electrode is configured to conduct high frequency alternating current from a generator to the patient tissue to cut, coagulate, dessicate, cauterize or fulgurate tissue in a preselected surgical site. The electrosurgical blade can degrade over time due to repeated use on human tissue. The performance of the electrosurgical blade can be compromised after a certain number of uses or after a certain time of use. Currently the performance of an electrosurgical blade is tested by a human operator such as a lab technician or an engineer or any other suitable operator. The operator will use the electrosurgical blade to cut a test material at a preset power setting. This testing process is subjective and the result is human dependent, i.e. the results are dependent on the actions performed by the operator. In research laboratories existing ball-on-disk or budding shear tests are used to determine the cutting performance of an electrosurgical blade. There is a need for a way to quantitatively and more objectively test the cutting performance of an electrosurgical tool, such as an electrosurgical blade to ensure optimal performance during surgery.

SUMMARY OF THE INVENTION

The present disclosure describes one or more embodiments of an apparatus for testing performance of an electrosurgical tool and a method of testing performance of an electrosurgical tool that will overcome or substantially ameliorate at least some of the deficiencies of the prior art, or at least provide the public with a useful alternative.

The present disclosure relates to an apparatus for testing the performance an electrosurgical tool and a method of testing the performance of an electrosurgical tool, in particular the present disclosure relates to an apparatus for testing the performance of an electrosurgical blade or cutter and a method of testing the performance of an electrosurgical blade or cutter. In particular the apparatus is a test rig or a test apparatus that is configured to allow a user to perform a controlled cut on a test material and evaluate the cutting performance of the electrosurgical blade and the non-stickiness of the electrosurgical blade. The apparatus is configured to allow a user to objectively determine the cutting performance of an electrosurgical blade.

In accordance with a first aspect, the present disclosure relates to an apparatus for testing performance of an electrosurgical tool comprising:
a frame, a clamp module coupled to the frame and configured to retain a test material in an selected orientation, and a tool module coupled to the frame and configured to grip an electrosurgical tool. The apparatus is configured to allow a user to perform a controllable cut to evaluate the cutting performance of the electrosurgical tool. The cutting performance is evaluated based on determining a resistance force between the electrosurgical tool and the test material as the electrosurgical tool performs the controllable cut and determining non-stickiness of the electrosurgical tool after the electrosurgical tool performs the controllable cut.

In an embodiment, the clamp module is coupled to the frame via a movement module, the clamp module is connected to the movement module, the movement module is moveably connected to the frame, and the movement module is moveable in a single plane.

In an embodiment, the frame comprises a base and an elongate rail spaced apart from the base, the movement module is moveably coupled to the elongate rail and configured to move in a single plane parallel to the longitudinal axis of the rail, and the movement of the movement module causes the clamp module to move along the rail.

In an embodiment, the movement module further comprises a servomotor and a carriage moveably coupled to the rail. The servomotor is coupled to the carriage and is configured to control the movement of the carriage along the rail.

In an embodiment, the apparatus further includes a load sensor being coupled to the tool module, wherein the load sensor is configured to measure the resistance force between the test material and the electrosurgical tool.

In an embodiment, the clamp module comprises a pair of clamps, the clamps are spaced apart from each other and moveable toward each other, and wherein the clamps are configured to grasp the test material in a stretched configuration, wherein the amount of stretch is adjusted based on the space between the clamps.

In an embodiment, each clamp comprises a pair of opposing jaws that can move between an open position and a closed position, wherein the pair of opposing jaws are configured to grip the test material when the jaws are in the closed position, and wherein at least one jaw includes a sawtooth surface, the sawtooth surface is configured to contact the test material and grip the test material when the jaws are in the closed position.

In an embodiment, the tool module comprises a holder and a runner, the holder is configured to rigidly retain the electrosurgical tool, and the runner is coupled to a portion of the frame and is configured to move in a single plane along a portion of the frame such that the tool module moves in a single plane relative to the frame.

In an embodiment, the runner and tool module are configured to move in a plane that is perpendicular to the plane of motion of the carriage and clamp module, wherein the motion of the tool module allows adjustment of a cutting depth of the electrosurgical tool.

In an embodiment, the frame further comprises a vertical beam extending perpendicular to the elongate rail, and the runner is coupled to the vertical beam and is moveable along the vertical beam, and the runner is coupled to an adjustment mechanism that is configured to allow incremental adjustment of the runner along the vertical beam.

In an embodiment, the tool module further comprises an adjustable bearing coupling the holder to the vertical beam, the adjustable bearing including an actuator configured to adjust the angular position of the bearing and holder relative to the vertical beam, the adjustable bearing being adjustable between a plurality of angular positions and the bearing allowing a user to adjust the angle of the electrosurgical tool within the holder.

In an embodiment, the clamp module includes a tension sensor, the tension sensor being in communication with the clamps and configured to determine the tension of the test material once the test material is retained by the clamps.

In an embodiment, the apparatus further comprises a generator, wherein the generator is a high frequency power or current generator that is configured to provide a high frequency power or current signal to the electrosurgical tool to energize the electrosurgical tool.

In an embodiment, the apparatus comprises a controller and an actuator, the actuator being in electronic communication with the controller and the actuator being manually actuable between a first position and a second position, the controller being in electronic communication with the generator and configured to activate the generator and supply to the electrosurgical tool when the actuator is in a first position and deactivate the generator and stop supply to the electrosurgical tool when the actuator is in a second position.

In an embodiment, the load sensor is an S beam load sensor or an optical sensor, wherein the load sensor is configured to determine a resistance force of the electrosurgical tool at a specific cutting depth, and the lower the resistance force the better the performance of the electrosurgical tool.

In an embodiment, the adjustment mechanism coupled to the runner is an electronic adjustment mechanism that is configured to move the runner relative to the frame, the electronic adjustment mechanism allowing predefined or incremental movement of the runner and the tool module relative to the frame.

In an embodiment, the apparatus comprises a controller in communication with the load sensor, the controller further includes an electronic processor that is configured to receive measurements from the load sensor, process the measurements from the load sensor and determine a resistance force between the test material and the electrosurgical tool.

In accordance with a second aspect, the present invention provides a method of testing the performance of an electrosurgical tool, the method comprising the steps of: positioning a test material in a clamp module, adjusting the clamp module to preload the test material to an initial preload, adjusting an electrosurgical tool to an initial height and an initial angle, activating power supply to the electrosurgical tool, moving the electrosurgical tool or test material in one or more planes on the test material to create a cut, and evaluating the cutting performance of the electrosurgical tool based on one or more measurements taken as the electrosurgical tool performs the cut or after the electrosurgical tool performs the cut.

In an embodiment, the step of adjusting the clamp comprises adjusting the clamp module to ensure the test material is under tension, and the step of moving the electrosurgical tool comprises moving the electrosurgical tool in a vertical plane relative to the test material to a cutting depth.

In an embodiment, the method further comprises moving the clamp module in a horizontal plane a predetermined distance such that the electrosurgical tool creates a cut in the test material.

In an embodiment, the step of evaluating the cutting performance comprises determining a resistance force versus a cutting depth of the electrosurgical tool for a single cut, the lower the resistance force the greater the cutting performance of the electrosurgical tool.

In an embodiment, the step of evaluating the non-stickiness of the electrosurgical tool includes measuring a final weight of the electrosurgical tool using a digital weight balance after the cut, determining a weight gain based on the measured final weight and an initial weight of the electrosurgical tool before the cut, and determining non stickiness based on the weight gain, wherein the smaller the weight gain the greater the non-stickiness of the electrosurgical tool.

The term "comprising" (and its grammatical variations) as used herein are used in the inclusive or open sense of "having" or "including" and not in the closed sense of "consisting only of".

BRIEF DESCRIPTION OF THE DRAWINGS

Embodiments of an apparatus for testing performance of an electrosurgical tool and a method of testing the performance of an electrosurgical tool will be described, by way of example, with reference to the accompanying drawings in which.

DETAILED DESCRIPTION OF AN EMBODIMENT

Electrosurgery is an increasingly used and adopted medical procedure. Electrosurgery involves the application of high frequency, alternating polarity, electrical current to biological tissue as a mechanism cut, coagulate, desiccate or fulgurate tissue within a human body. The high frequency, alternating polarity, electrical current is applied to tissue via an electrosurgical tool, such as for example an electrosurgical blade. The amplitude and frequency of the electrical current is predefined depending on the type of operation being performed and one or more patient parameters such as patient age, weight or operation location and so on.

Figure 1A:
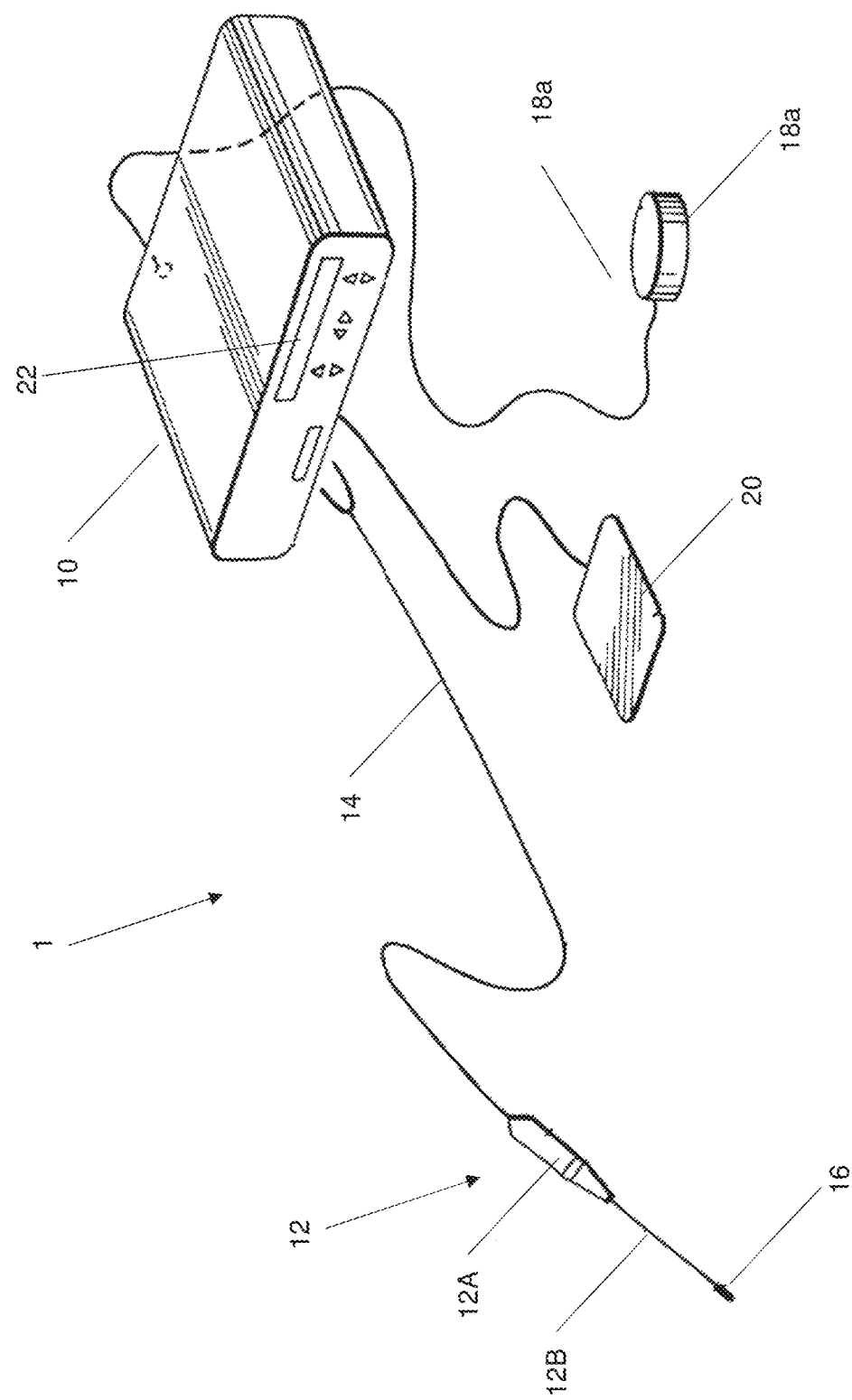
FIG. 1a shows an electrosurgical system that comprises an electrosurgical tool and a generator.

FIG. 1a shows an electrosurgery system 1. The electrosurgery system comprises a generator 10 that provides a high frequency power or current output to an electrosurgical tool 12. Preferably the generator 10 is configured to generate a high frequency current output. The generator 10 is a generator that generates high frequency, alternating electrical current that is delivered to the electrosurgical tool 12 via a connection cord 14. The current is used to heat an electrode assembly 16 in the electrosurgical tool 12. The heated electrode 16 can be used to cut, cauterize, coagulate, desiccate or fulgurate tissue within the human body. To minimize the effects of muscle or neural stimulation the electrosurgical system typically operates in the radio frequency (RF) range of 100 kHz to 5 MHz. The generator 10 is configured to generate electrical current in the RF range. Alternatively the generator 10 may generate an electrical current at a very high frequency (VHF) or ultra high frequency (UHF) such as for example between 300 MHz to 10 GHz, and preferably above 1 GHz. Generally these frequencies of operation are above frequencies that would affect muscles or nerves. Operation at higher frequencies also helps to minimize the amount of hydrogen and oxygen generated by electrolysis of water in the body.

The electrosurgical tool 12 is mounted on a handpiece 12A that is configured to grasped by a user such as a surgeon. The handpiece 12A is shaped for easy and comfortable gripping by the user. The tool 12 includes shaft 12B that connects to the electrode assembly 16 at a distal end of the shaft 12B. The shaft is coupled to the handpiece 12A at a proximal end of the shaft 12B. The shaft 12B acts a feed structure for the electrode assembly 16. The shaft 12B is a rigid co-axial tube having an inner conductor and an outer supply conductor. The shaft 12B may be made from a metal or a plastics material with a metallic coating. The electrode assembly 16 may comprise one or more electrodes. In one example the electrode assembly 16 comprises an active electrode and a return electrode. The active electrode and return electrode together constitute an axially extending dipole. The dipole is dimensioned to match the load represented by the tissue and air current path to the characteristic impedance of the feed structure, i.e. the shaft 12B. The electrode assembly 16 may comprise an insulating sheath (not illustrated) which covers the shaft 12B and terminates in a ceramic insulator at the proximal end of the shaft 12B.

The electrosurgery system 1 further comprises a return path 18 that is provided for the electrical current provided to the tissue via the tool 12. The return path 18 may be in a monopolar or bipolar circuit. The system 1 may comprise a return pad or a return electrode. A return pad is often used in a monopolar circuit and the pad is in contact with the patient. A return electrode is used in a bipolar circuit and is connected to the electrosurgical tool 12. The return path 18 is connected to receive at least a portion of the transmitted electrosurgical energy (the delivered current) from the generator 10 and then the patient. The generator 10 includes a return input that receives and connects to the return path 18. The return path 18 may be a cord or electrical conductor. In the illustrated example the return path is a monopolar path that includes a contact element 18a that is positioned in contact with the patient. The system further comprises an actuator 20. The actuator 20 is configured to allow a user, such as a surgeon, to activate the supply of current, i.e. the electrosurgical energy. In the illustrated example the actuator 20 is a pedal. The pedal is foot actuated and is in electrical communication with the generator 10 and the electrode 16 to control supply of current to the electrode 16. The actuator 20 is in electrical communication with the generator 10. Alternatively the actuator 20 may be a switch or button located on the handpiece of 12A or a separate hand actuated button.

The generator 10 further comprises a user interface 22. The user interface communicates information regarding the operation of the electrosurgery system 1, and in particular the operation or function of the generator 10. The user interface 22 may comprise a LCD screen or LED screen and a plurality of input devices such as buttons or knobs. The input devices allow a user to modify various parameters of the generator such as the amplitude of the current or frequency of current supplied. The user interface 22 may alternatively comprise a touch screen that communicates information to the user but also allows a user to input information. The user can modify the operating mode via the user interface. For example the user may set the generator 10 to operate in "cut" mode or "coagulate" mode or "fulgurate" mode etc. These modes may comprise pre-set or predefined power levels (i.e. current and voltage levels) that are delivered to the electrosurgical tool 12.

Figure 1B:
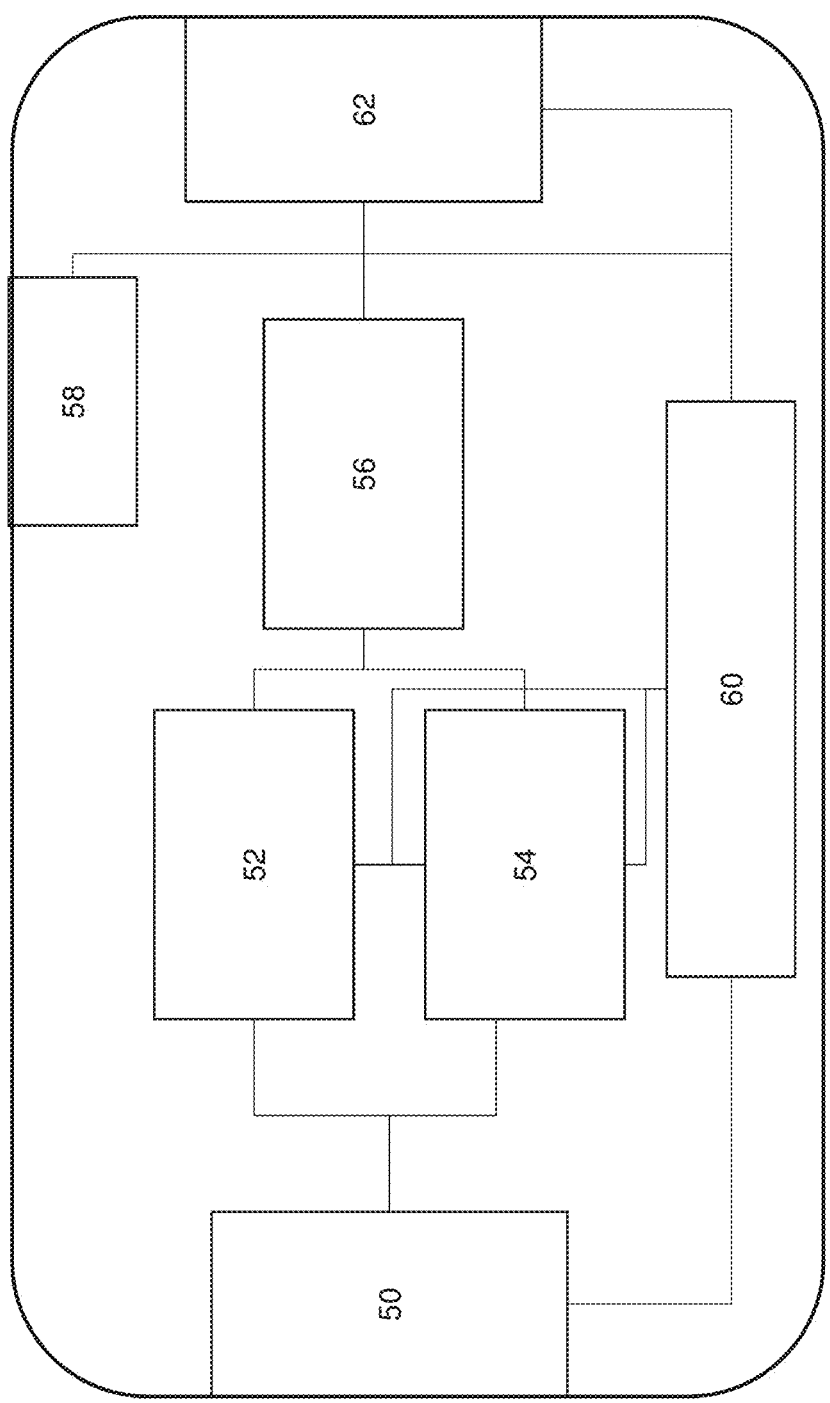
FIG. 1b shows an internal schematic of the generator of the electrosurgical system.

The generator 10 comprises suitable electronic components that allow the function of the generator 10. FIG. 1b shows a schematic diagram of the internal components of the generator 10. FIG. 1b is an exemplary embodiment of the internal components of the generator 10. The internal components of the generator 10 are shown as a block diagram in FIG. 1b. The generator 10 comprises a power supply 50, a modulator 52, an oscillator 54, a filter 56, an I/O interface 58 and a controller 60. The controller 60 is in electrical communication with one or more components of the generator 10 and is configured to control the operation of any or more of the components of the generator.

The power supply 50 receives AC input power from power supply lines. The power supply 50 may receive power from a wall source or any other suitable power generator. The power supply 50 comprises a plurality of active electrical lines, a neutral line and may optionally include a ground line. The power supply 50 is configured to supply an AC current or an oscillating current. The power supply 50 may also be configured to receive a DC current and supply a DC current.

The oscillator 54 is in electrical communication with the power supply 50. The oscillator 54 is configured to modify the frequency of the oscillating or alternating current. The oscillator 54 is also configured to create an oscillating current if a DC or direct current is received from the power supply 50. The oscillator 54 comprises suitable electronic components that may be arranged on a board or as an integrated circuit. In some instances the oscillator 54 may let the current through with no modification. Operation of the oscillator may be defined or controlled by the controller 60.

The modulator 52 is in electrical communication with the power supply 50. The modulator 52 may also be in communication with the oscillator 54. The modulator 52 is configured to modulate the amplitude of the voltage that is supplied to the electrosurgical tool 12. The modulator 52 is also configured to control the amplitude of the current delivered to the electrosurgical tool 12. The modulator 52 is configured to increase or decrease the amplitude of the current or voltage or both to affect the power delivered via the tool 12. The modulator 52 comprises suitable electronic components arranged in a suitable manner such as an integrated circuit. The modulator 52 is in communication with the controller 60 that controls the operation of the modulator 52.

The generator 10 further comprises a filter 56. The filter 56 is in electrical communication with the modulator 52 and oscillator 54. The filter 56 is any suitable filtering arrangement. The filter 56 may be a capacitor or a plurality of capacitors or an LC circuit or an RLC circuit or any other suitable filtering circuit arrangement. The filter 56 may alternatively be comprised of semiconductor components such as transistors or Triacs or Opamps or any other suitable components. The filter 56 is configured to filter the output of the modulator 52 and oscillator 54. The modulator 52 and oscillator 54 outputs are combined into a single line that is sent to the filter 56. The filter 56 is configured to smooth the current and voltage delivered to the tool 12. The filter 56 is also configured to filter noise from the current signal, voltage signal or both that is delivered to the tool 12. The filter 56 is a provided as a preset filter in a suitable arrangement such as an integrated circuit. Alternatively the filter 56 may be a dynamic filter that is actively controlled by the controller 60. The controller 60 may be configured to change the filtering criterion that is applied by the filter 56.

The filter is connected to an output interface 62. The output interface comprises suitable interfacing circuitry that allows transmission of power along the connection cord 14. The output interface may be positioned in a socket or connector disposed on the generator 10.

The I/O interface 58 is in electrical communication with the user interface 22. The I/O interface 58 is configured to receive information from the user interface 22 and transmit information to the user interface 22. The I/O interface 58 is a hardware module with suitable electronic components. Further the I/O interface 58 is in communication with the controller 60. The controller 60 is configured to control various operations based on user inputs via the user interface 22. For example the controller 60 is configured to increase the frequency of the delivered current, or increase the amplitude of the current or switch off the current and so on. The I/O interface 58 comprises suitable electronic components in any suitable arrangement. For example the I/O interface 58 may be an integrated circuit package.

The controller 60 is configured to control the operations and functions of the generator 10. Specifically the controller 60 is arranged in electronic communication with the other components of the generator 10. The controller 60 is a suitable electronic controller such as a microcontroller. The controller 60 includes at least a processor and interfacing circuitry that allows the controller to electronically communicate with the other components of the generator 10. The controller 60 may include embedded memory, wherein the memory is a read and write memory. The memory on the controller may be a solid state memory or a flash memory unit. The controller memory 60 may allow a user to store information such as operational modes, commonly used frequency or amplitude settings and so on. In an alternative form the generator 10 may include a memory block (not illustrated) that is in electronic communication with the controller 60. This memory block may be ROM, RAM, flash memory or a solid state drive. The memory block may be a hardware memory block that is a read and write memory block. The memory block allows the generator to store user preferences or operating modes or operating settings.

As disclosed earlier an electrosurgical tool 12, in particular an electrosurgical blade can degrade over time due to repeated use on human tissue. The blade 12 is subject to high temperature during use. This high temperature causes proteins, lipids, and carbohydrates from the body to adhere to the working tip of the blade, in particular on the electrode section of the electrosurgical blade 12. This build of proteins, carbohydrates, lipids and other tissue fragments can reduce the cutting efficiency of the electrosurgical blade and also can require the user to use a higher current or power during operation. Under such high power conditions eschar can be built easily. The built up tissue on the electrosurgical blade 12 can also lead to surgical fires, since the built up tissue can act as a fuel source. Typically surgeons can replace the electrosurgical tool 12 or blade with a new one. However this adds to the overall cost of surgery. There have been developments made to reduce the stickiness and improve the wear resistance of the electrosurgical blade 12. Non stickiness can be achieved using several techniques. Some commonly used techniques are by applying low surface energy coatings or creating surface roughness on the blade or by applying hydrophobic materials to portions of the blade. The cutting performance of the blade can be improved by using these techniques.

Currently there is no apparatus for testing the performance of an electrosurgical tool. In particular there is no apparatus, such as a test rig, to test the cutting performance of an electrosurgical tool such as an electrosurgical blade. Currently the measurement of the non-stick property of the electrosurgical blade is usually carried out by using the electrosurgical blade to cut a test material, such as for example a portion of a pig carcass or synthetic materials that simulate human tissue. Pig carcasses are often used since pig tissue most closely resembles human tissue in structure and behavior. The electrosurgical blade is operated at a preset power setting. The effectiveness of the cutting and user friendliness is recorded by an operator. The amount of tissue stuck to the electrosurgical blade is determined using a digital weight balance. This process is subjective and the result is by and large human dependent. Alternatively a ball-on-disk or budding shear tests can be used in a laboratory setting to determine non-stickiness and wear on an electrosurgical blade. It is however difficult to obtain accurate cutting performance of the blade by using two separated tests. There is a need for an apparatus that can allow an operator to objectively test the performance of an electrosurgical tool, in particular the cutting performance of an electrosurgical blade.

The present disclosure is directed to an apparatus for testing the performance of an electrosurgical tool and in particular an apparatus for testing the cutting performance of an electrosurgical blade. The apparatus is advantageous because it allows repeatable, reliable and quantitative results of cutting performance. The apparatus for testing the cutting performance of an electrosurgical blade is also advantageous because it provides a device to objectively test the cutting performance of various electrosurgical blades and allow comparison as well as replacement of underperforming or worn blades.

Figure 2A:
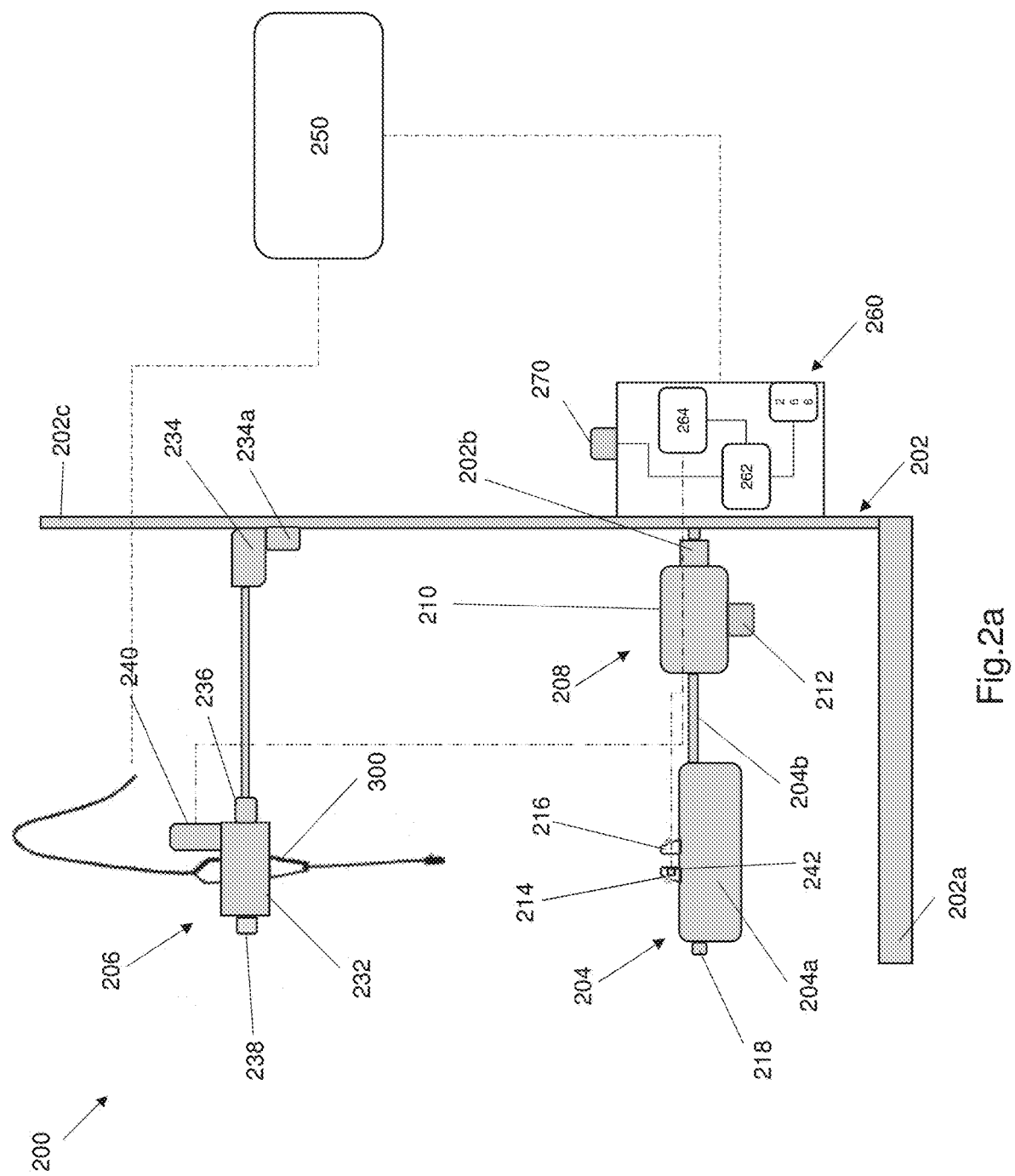
FIG. 2a shows a front view of the apparatus for testing performance of an electrosurgical tool.
Figure 2B:
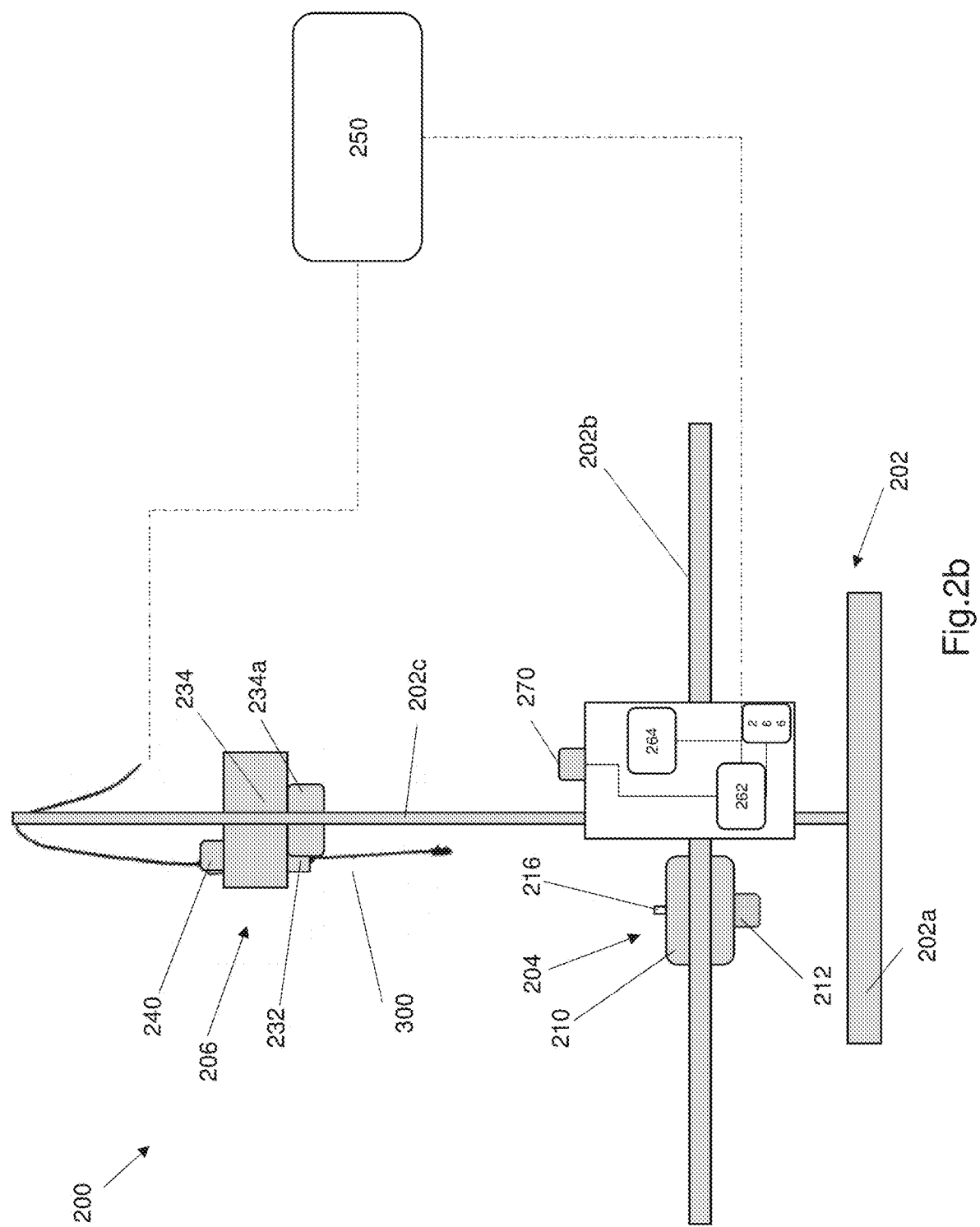
FIG. 2b shows a side view of the apparatus for testing performance of an electrosurgical tool.

FIGS. 2a and 2b show an embodiment of an apparatus for testing the performance of an electrosurgical tool. In particular FIGS. 2a and 2b show an embodiment of a test rig that can be used to test the cutting performance of an electrosurgical blade. FIG. 2a shows a front or side view of the testing apparatus 200. FIG. 2b shows an end view of the testing apparatus 200 shown in FIG. 2a. Referring to FIG. 2a, the testing apparatus 200 comprises a frame 202, a clamp module 204 and a tool module 206. The frame 202 is a rigid structure that may be formed from—a rigid insulating polymer material. The frame 202 provides a rigid mounting structure for the various components of the testing apparatus 200. The clamp module 204 is configured to retain a test material in a selected orientation. The clamp module 204 is coupled to the frame 202. The tool module 206 is coupled to the frame 202 and configured to grip an electrosurgical tool 300. The apparatus 200 is configured to allow a user to perform a controllable cut to evaluate the cutting performance of the electrosurgical tool. The cutting performance is determined based on the resistance force between the electrosurgical tool and the test material, and the non-stickiness of the electrosurgical tool. The testing apparatus 200 is particularly suited for testing the performance of an electrosurgical blade. The testing apparatus 200 will be described with respect to an electrosurgical blade.

The clamp module 204 is coupled to the frame via a movement module 208, wherein the clamp module 204 is connected to the movement module 208. The movement module 208 is moveably connected to the frame and wherein the movement module 208 is moveable in a single plane. The clamp 204 moves in a single plane due to the movement of the movement module 208. The clamp module 204 may be rigidly connected to the movement module 208. Alternatively the clamp module 204 may be pivotably connected to the movement module 208 such that the angular orientation of the clamp module 204 relative to the movement module 208 or frame can be adjusted by the user. The clamp module 204 may be connected to the movement module 208 by any suitable pivoting connector such as for example a hinge or a spool connection or any other suitable connector. The pivoting connector allows the angle of the clamp module 204 to be varied. A pivoting connector is arranged for manual actuation by a user to adjust the angular orientation of the clamp module 204.

The frame 202 includes a base 202a that provides a stable platform for the apparatus 200. As shown in FIG. 2a the base 202a includes a flat plate that can rest upon a test bench or any other suitable location the apparatus is used on. Alternatively the base 202a may also include two or more feet connected to the flat plate. The frame comprises an elongate rail 202b that is spaced apart from the base. The elongate rail 202b extends horizontally. The elongate rail 202b has a square cross section. Alternatively the elongate rail 202b may include any other suitable cross section. The frame 202 further comprises vertical beam 202c. The vertical beam 202c extends perpendicular to the elongate rail 202b. The vertical beam 202c has a rectangular cross section. Alternatively the vertical beam 202c has a circular cross section or an elliptical cross section.

The movement module 208 is moveably coupled to the elongate rail 202b and is configured to move in a single plane, wherein the single plane of motion is parallel to a longitudinal axis of the elongate rail 202b. The movement of the movement module 208 along the elongate rail causes the clamp module 204 to move along the rail or relative to the rail 202b.

The movement module 208 comprises a carriage 210. The movement module 208 further comprises a servomotor 212 that is coupled to the carriage 210. The servomotor 212 is configured to control the movement of the carriage 210 along the elongate rail 202b. The carriage 210 is moveably coupled to the elongate rail 202b via any suitable moveable element. In one example the carriage 210 includes a wheel (not illustrated) that is located in a slot in the elongate rail 202b and is moveable along the rail 202b. Alternatively the wheel of the carriage 210 may be located on top of the elongate rail 202b and moveable along the rail 202b. The servomotor 212 allows a user or a controller to controllably move the carriage along the rail 202b. The servomotor 212 also allows incremental movement of the carriage 210 along the elongate rail 202b.

The clamp module 204 is connected to the movement module 208 via an elongate strut 204b. The clamp module 204 further comprises a body 204a with a flat upper surface. The body 204a is a rigid body and can function as a test bed for retaining the test material. The clamp module 204 comprises a pair of clamps 214, 216 that are mounted on the upper surface of the body 204a. The clamps 214, 216 are spaced apart from each other and moveable toward each other, and wherein the clamps 214, 216 are configured to grasp the test material in a stretched configuration. The clamps 214, 216 are also spaced upwardly away from the upper surface of the clamp module body 204a. The amount of stretch of the test material is adjusted based on the space between the clamps 214, 216. The amount of stretch corresponds to an initial preload of the test material. The test material is preloaded in tension. The clamps 214, 216 are mounted on a threaded, linear adjustment mechanism 218 that allows the clamps to move linearly relative to each other. The threaded linear adjustment mechanism 218 may be a horizontal screw or a rack and pinion mechanism that can be adjusted by the user to adjust the tension preload of the test material. Alternatively one clamp may be stationary and the other clamp is moveably mounted using a rack and pinion mechanism or any other linear movement or linear adjustment mechanism. The linear adjustment mechanism allows incremental adjustment of the clamps, thus allowing linear adjustment of the tension on the test material.

Figure 2C:
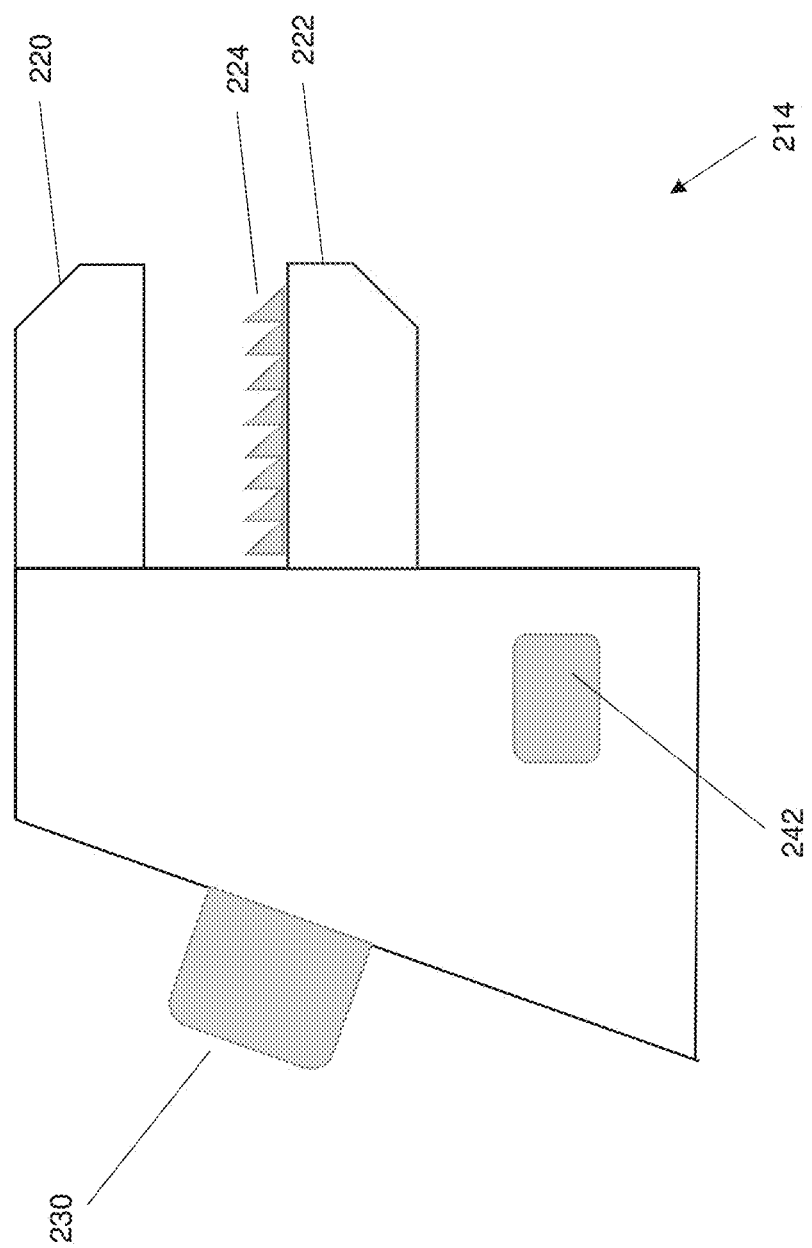
FIG. 2c shows a side view of one clamp from the clamp module that includes a pair of jaws for gripping a test material.

Each clamp comprises a pair of opposing jaws. FIG. 2c shows a close up view of single clamp 214 of the clamp module 204. Each clamp 214, 216 of the clamp module has a structure similar to that shown in FIG. 2c. Referring to FIG. 2c, the clamp comprises a pair of opposing jaws 220, 222. The jaws 220, 222 can move relative to each other. The jaws 220, 222 can move between an open position and a closed position. FIG. 2c shows the jaws 220, 222 in an open position. The opposing jaws 220, 222 are configured to grip the test material when the jaws 220, 222 are in a closed position.

At least one jaw includes a sawtooth surface. As shown in FIG. 2c, the lower jaw 222 has a sawtooth surface 224. The sawtooth surface 224 comprises a plurality of sawtooth protrusions 226, as shown in FIG. 2c. The sawtooth protrusions are microstructures that are integral to the jaw and formed in the jaw. Alternatively the sawtooth protrusions may be located on a separate tape that is applied to the jaw. The sawtooth surface is configured to contact the test material and grip the test material when the jaws are in the closed position. The sawtooth surface helps to grip the test material in use and improves the grip of the jaws.

The clamp includes an adjustment element 230 that is configured to allow adjustment of one or both jaws. The adjustment element allows the jaws to be moved toward or away from each other in a single plane of motion, such as for example a vertical plane of motion. The motion of the jaws may be parallel to the motion of the tool module 206. The adjustment element 230 may take any suitable form and can include any suitable adjustment mechanism. FIG. 2c shows an adjustment knob 230 that functions as the adjustment mechanism. The adjustment knob 230 being rotatable to adjust the position of jaws to grip the test material or loosen the test material.

The tool module 206 is coupled to a portion of the frame 202 and is configured to move along the frame in a single plane. The tool module 206 is configured to move in a plane that is perpendicular to the movement of the clamp module 204. The tool module 206 is configured to move in or along a vertical plane of motion.

The tool module 206 comprises a holder 232 that is configured to rigidly retain the electrosurgical tool 300. The holder 232 is configured to rigidly retain the electrosurgical tool such that the tool does not rattle or move too much within the holder 232. The tool module 206 further comprises a runner 234 that is connected to a portion of the frame. The runner 234 is connected to the holder 232. The runner 234 is also coupled to the vertical beam 202c and is configured to move in a single plane along the vertical beam 202c such that the tool module 206 moves in a single plane along the vertical beam 202c. The runner 232 and tool module 206 are configured to move in a plane that is perpendicular to the plane of motion of the carriage 210 and clamp module 204, wherein the motion of the tool module 206 allows adjustment of a cutting depth of the electrosurgical tool 300.

The tool module 206 comprises a rigid rod 234a that connects the runner 234 and the holder 232. The holder 232 further comprises an adjustable bearing 236 coupling the holder 232 to the vertical beam 202c. The adjustable bearing 236 interconnects the rigid rod 234a and the holder 232 such that the holder and pivot or rotate about the rigid rod 234a, thereby adjusting the angle of the holder relative to the vertical beam 202c. The adjustable bearing 236 includes a manual actuator 238 that is configured to adjust the angular position of the bearing 236 and the holder 232 relative to the vertical beam 202c. The adjustable bearing 236 is manually adjustable between a plurality of angular positions and the bearing allows a user to adjust the angle of the electrosurgical tool 300 relative to the vertical beam 202c.

The cutting performance of an electrosurgical tool is determined based on a resistance force between the test material and the electrosurgical tool. The testing apparatus 200 further comprises a load sensor 240, the load sensor 240 is being coupled to the tool module 206 and wherein the load sensor 240 is configured to measure the resistance force between the test material and the electrosurgical tool 300. The load sensor 240 is an S beam load sensor that is configured to determine a resistance force of the electrosurgical tool at a specific cutting depth. The lower the resistance force the better the performance of the electrosurgical tool. Alternatively the load sensor may be an optical sensor or a strain gauge or any other suitable load sensor. Alternatively the load sensor 240 may be coupled to the clamp module 204.

The clamp module 204 includes a tension sensor 242, the tension sensor being in communication with the clamps 214, 216 and configured to determine the tension of the test material once the test material is retained within the clamps 214, 216. FIG. 2c shows a tension sensor mounted on a clamp. Alternatively the tension sensor 242 may be mounted on the body of the clamp module. The test material can be any suitable material that behaves or simulates human tissue. In one example, the test material may be an animal tissue material such as pig tissue. This may be preferable in some instances as pig tissue most closely simulates human tissue. In a further alternative the test material may be human tissue that can be appropriately sourced.

The testing apparatus 200 further comprises components of an electrosurgery system. The testing apparatus 200 comprises a generator 250. The generator 250 is high frequency power or current generator that is configured to provide a high frequency power or current signal to the electrosurgical tool within the testing apparatus 200 to energize the electrosurgical tool 300. The apparatus 200 for testing the performance of an electrosurgical tool also comprises a controller 260 and an actuator 270. The actuator 270 is in electronic communication with the controller 260 and is manually actuable between a first position and a second position. The controller 260 is in electronic communication with the generator 250. The controller 260 is configured to activate the generator and supply a power or current signal to the electrosurgical tool when the actuator is in the first position. The controller 260 is configured to deactivate the generator and stop supply of a power or current signal to the electrosurgical tool 300 when the actuator 270 is in a second position. The controller 260 includes an outer casing that contains all the controller constituents. The controller 260 may be mounted on the frame 202.

The controller 260 is in electronic communication with the load sensor 240 and the tension sensor 242. The controller 260 comprises an electronic processor 262 that is configured to receive measurements from the load sensor 240, process the load sensor measurements and determine the resistance force between the test material and the electrosurgical tool. The electronic processor 262 is a hardware processor with electronic components arranged to perform various processing tasks. The processor 262 is arranged as an integrated circuit and may be a single core or multiple core processor, such as for example an AMD Athlon X2 or a LGA 775 or an FPGA device or any other suitable microprocessor. The controller 260 also includes a memory unit 264 that is electronically connected to the processor. The memory unit 264 may be a hardware memory unit such as a solid state drive or ROM or RAM or flash memory. The memory unit 264 can permanently or temporarily store information such as a plurality of load sensor measurements. The memory unit 264 also stores computer instructions in the form of executable software. The processor 262 is configured to execute the stored software (i.e. the computer instructions) in order to perform various tasks such as determine the resistance force based on load sensor measurements. The controller 260 includes a user interface 266 to communicate information such as the resistance force and initial tension on the test material to the user. The information is communicated graphically or visually to the user and may also be communicated audibly to the user.

The runner 234 is coupled to an adjustment mechanism 234a that is allowed to vertical adjustment of the runner along the vertical beam. The adjustment mechanism 234a is configured to allow incremental adjustment of the runner, and the holder along the vertical beam. The adjustment mechanism 234a is an electronic adjustment mechanism that is configured to move relative to the frame and in particular the vertical beam. The electronic adjustment mechanism 234a allows predefined or incremental movement of the runner 234 and the tool module 206 relative to the frame, in particular the vertical beam. The vertical position of the tool module 206 may be controlled by the controller 260. A user may input a predefined vertical position, wherein the predefined vertical position of the tool module 206 corresponds to an initial cut depth by the electrosurgical tool. The controller 260 is configured to send a signal to the electronic adjustment mechanism 234a to lower the tool module 206 to a specified height by the user. The signal is preferably a wireless signal but alternatively a wired connection can exist between the controller 260 and the adjustment mechanism 234a. The controller 260 is configured to record the initial cutting depth of the tool, i.e. how far the tool is lowered by the electronic adjustment mechanism 234a. The initial cutting depth is user defined for a specific test. The initial cutting depth is stored in the memory unit 264 or may be displayed on the user interface 266.

The controller 260 is further configured to control the horizontal movement of the clamp module 204. The controller 260 can send a signal to the servomotor 212 to incrementally move the clamp module 204 along the horizontal rail 202b. The servomotor 212 is in wireless communication with the controller 260. Alternatively the servomotor 212 may be connected to the controller by a wire. The horizontal movement of the clamp module 204 simulates a horizontal cut by the tool 300. The test cut performed by the testing apparatus 200 includes an initial cutting depth defined by the vertical position of the tool module 206 and a horizontal cut length defined by the horizontal movement of the clamp module. The controller 260 is configured to store the horizontal distance the clamp module moves due to servomotor actuation.

The apparatus for testing the performance of an electrosurgical tool 200 is used by a user to perform a method 400 of testing the performance of an electrosurgical tool. The method of testing performance is used to test the cutting performance of an electrosurgical tool. The electrosurgical tool is an electrosurgical blade that is used to cut tissue. The method can be carried out by any suitable user such as a lab technician or a quality engineer or a repair technician or any other suitably qualified individual.

Figure 3:
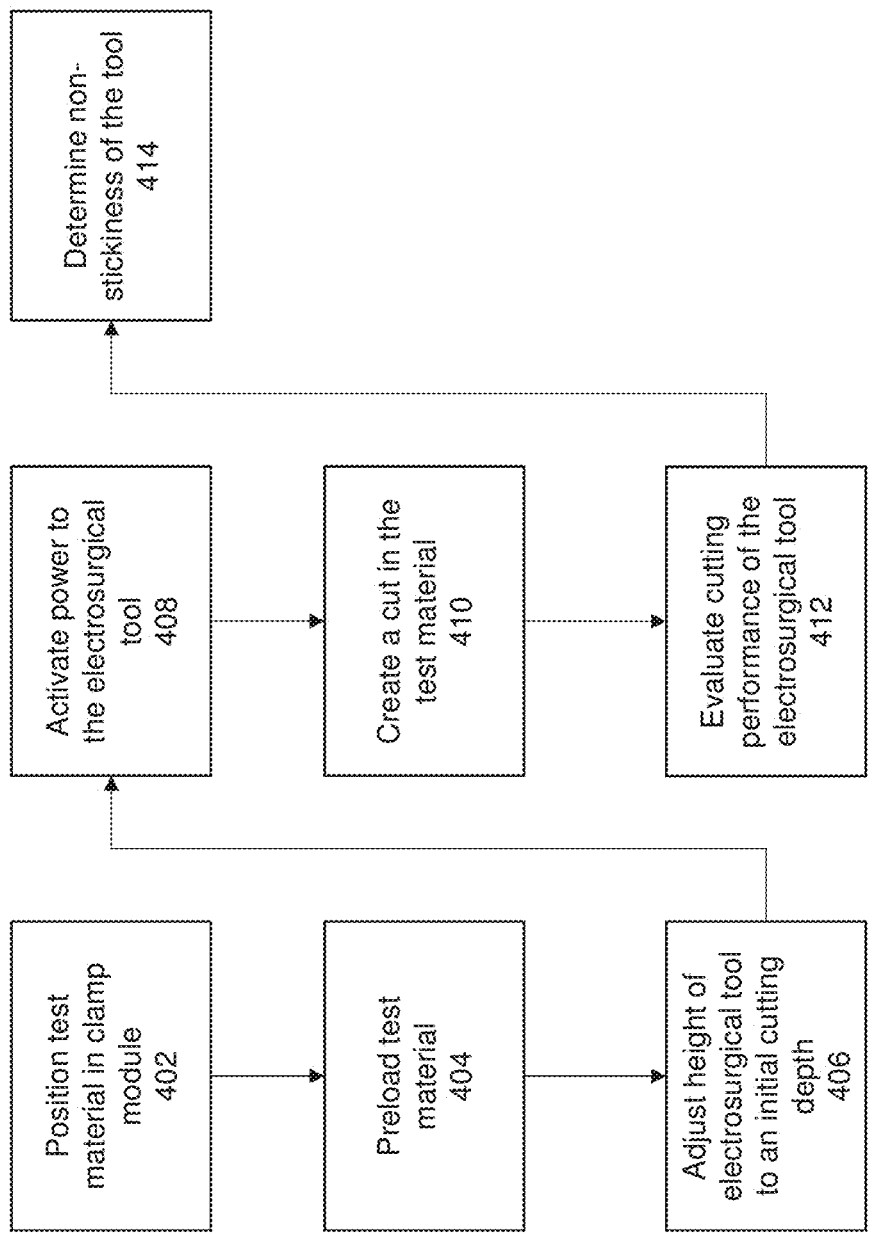
FIG. 3 shows a flow chart for a method of testing the performance of an electrosurgical tool.

The method 400 of testing performance of an electrosurgical tool is illustrated in FIG. 3. FIG. 3 shows a flow chart defining the method steps. The flow chart and method of testing performance shown in FIG. 3 is an embodiment of the method of testing the performance of an electrosurgical tool. Referring to FIG. 3, the method begins at step 402. Step 402 comprises positioning a test material in a clamp module of the testing apparatus 200. Step 404 comprises adjusting the clamp module to preload the test material with an initial preload. The initial preload is preferably a tension load that is sensed by the tension sensor 242. The initial tension may be recorded by the controller 260 or displayed to the user or both. The method proceeds to step 406. Step 406 comprises adjusting an electrosurgical tool 300 to an initial height and initial angle. The height of the electrosurgical tool is adjusted by moving the adjustment mechanism 234a along the vertical beam 202c. The angle of the tool 300 is adjusted by manipulating the actuator 238 to adjust the bearing 236 which thereby adjusts the angular position of the holder 232. Step 408 comprises activating a power supply to the electrosurgical tool 300. The power is supplied by the generator 250. Step 410 comprises moving the electrosurgical tool or test material in one or more planes on the test material to create a cut. Step 412 comprises evaluating the cutting performance of the electrosurgical tool based on one or more measurements.

The step 412 of evaluating the cutting performance comprises determining a resistance force versus a cutting depth of the electrosurgical tool for a single cut, the lower the resistance force the greater the cutting performance of the electrosurgical tool. The one or more measurements are measurements of the resisting force between the tool and the test material. The resistance force measurements are measured using the load sensor 240 and the controller is configured to process the load measurements and generate a performance value or display the resistance force for a cut. This method can be repeated for multiple electrosurgical tools and the performance of each tool is determined based on the resistance force and the non-stickiness of the tool. The lower the resistance force of a cut, the better the performance of the tool.

The method 400 may include the additional optional step of determining non-stickiness of a tool 414 following the step of moving the tool to create a cut in the test material. Non-stickiness of a tool is determined by measuring a weight of the tool after performing the cut and comparing the weight with an initial weight before performing the cut in the test material. The difference in weight is a measure of non-stickiness wherein the lower the difference in weight the greater the non stickiness of the electrosurgical tool.

The method 400 may include some of the following additional optional steps. Step 404 includes adjusting the clamp module to ensure the test material is under tension. The amount of tension is measured by the tension sensor. The initial tension of the test material is predefined based on the type of material and the type of tool being tested. Step 406 further comprises initially moving the electrosurgical tool in a vertical plane relative to the test material to an initial cutting depth. The initial cutting depth is recorded by the controller 260. The initial cutting depth can be predefined or preset by the user. The initial cutting depth is achieved by adjusting the height of the holder and tool module 206 by adjusting the position of the runner 234 relative to the vertical beam 202c.

Step 410 comprises moving the clamp module 204 in a horizontal plane a predetermined distance such that the electrosurgical tool 300 creates a cut in the test material. The clamp module 206 is moved horizontally by actuating the servomotor 212 to move the carriage 210 along the rail 202b. The distance of the cut is defined by the user. The load sensor 240 measures the resistance force as the cut is created. The step of evaluating the cutting performance comprises determining a resistance force versus a cutting depth of the electrosurgical tool for a single cut, the lower the resistance force the greater the cutting performance of the electrosurgical tool.

In an alternative embodiment the tool module 204 may comprise an articulating arm. The articulating arm allows the tool module 204 and the tool 300 to be moved in multiple planes of motion. In this alternative embodiment the articulating arm comprises four or more degrees of freedom of movement. Preferably the articulating arm connecting the tool module 204 to the frame 202 includes six degrees of freedom. The arm is configured to allow a user to move the tool 300 in at least a vertical plane and a horizontal plane separately or simultaneously. The articulating arm comprises one or more hinges to achieve the motion. Further articulating arm will comprise a plurality of electronically controllable actuators such as servomotors that are configured to control portions of the arm to achieve the desired motion. The arm can be articulated to move the electrosurgical tool to an initial cutting depth and then articulated to create a horizontal or angled cut along the test material. The arm comprises at least two joints. Both joints are ball joints but may be hinges. The first ball joint allows articulation to bring the tool to the initial depth. The second joint allows articulation to create a cut in a horizontal direction. The clamp module may be mounted on a stationary plate that extends from the frame. In this alternative embodiment the clamp module remains stationary and does not move through the cutting process since the articulating arm causes the required motion of the electrosurgical tool.

The presently described apparatus for testing the performance of an electrosurgical tool is advantageous because it provides an objective manner of testing performance of one or more electrosurgical tools. The apparatus is also advantageous because it allows measurement based comparison of performance rather than a subjective analysis. The testing rig or testing apparatus is further advantageous because the load sensor is accurate to 1 mN of force measurements. This provides the user with a high resolution of resistance force measurements. The testing apparatus as described herein is also advantageous because it allows a user to perform a controllable or controlled cut in order to evaluate cutting performance of an electrosurgical tool. The apparatus for testing is also able to simulate the cutting process carried out by surgeons by varying cutting speed, cutting length and cutting depth. The cutting speed and length can be varied by controlling the motion of the clamp module by controlling servomotor. The cutting depth is controlled by controlling the vertical position of the tool module by controlling the position of the runner and the adjustment mechanism associated with the runner. The testing apparatus and the method of testing performance as described herein provides a user with a standardized way of testing the performance of various electrosurgical tools and provides an easy way to accurately determine the cutting performance of each electrosurgical tool used.

It will be appreciated by persons skilled in the art that numerous variations and/or modifications may be made to the testing apparatus and method of testing performance of an electrosurgical tool, as described and shown in the specific embodiments without departing from the spirit or scope of the present disclosure. The present embodiments are, therefore, to be considered in all respects as illustrative and not restrictive.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof. As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, any other country.

The invention claimed is:

1. An apparatus for testing performance of an electrosurgical tool, the apparatus comprising;
    a frame;
    a clamp module coupled to the frame and configured to retain a test material in an selected orientation; and
    a tool module coupled to the frame and configured to grip an electrosurgical tool,
    wherein the apparatus is configured to allow a user to perform a controllable cut on the test material to evaluate a cutting performance of the electrosurgical tool based on (a) a resistance force between the electrosurgical tool and the test material as the electrosurgical tool performs the controllable cut and (b) a non-stickiness of the electrosurgical tool after the electrosurgical tool performs the controllable cut.

2. The apparatus of claim 1, further comprising a movement module, wherein the movement module is connected with the clamp module and is movably connected to the frame so as to couple the clamp module to the frame, and wherein the movement module is moveable in a single plane.

3. The apparatus of claim 2, wherein the frame comprises a base and an elongate rail spaced apart from the base, the elongate rail having a longitudinal axis;
    wherein the movement module is moveably coupled to the elongate rail and is configured move in the single plane, wherein the single plane is parallel to the longitudinal axis of the rail, and
    wherein movement of the movement module causes the clamp module to move along the elongate rail.

4. The apparatus of claim 3, wherein the movement module further comprises a servomotor and a carriage, and the carriage is moveably coupled to the elongate rail, and the servomotor is coupled to the carriage and configured to control movement of the carriage along the elongate rail.

5. The apparatus of claim 1, further comprising a load sensor coupled to the tool module and configured to measure the resistance force between the test material and the electrosurgical tool.

6. The apparatus of claim 5, wherein the load sensor is an S beam load sensor or an optical sensor, wherein the load sensor is configured to determine a resistance force of the electrosurgical tool at a specific cutting depth of the test material, and wherein the lower the resistance force the better the performance of the electrosurgical tool.

7. The apparatus of claim 5, further comprising a controller in communication with the load sensor, the controller further comprising an electronic processor configured to receive measurements from the load sensor, process the measurements from the load sensor, and determine a resistance force between the test material and the electrosurgical tool.

8. The apparatus of claim 1, wherein the clamp module comprises a pair of clamps spaced apart from each other and moveable toward each other, and wherein the pair of clamps are configured to grasp the test material in a stretched configuration, and wherein the amount of stretch of the test material by the pair of clamps is adjustable by changing an amount of space between the pair of clamps.

9. The apparatus of claim 8, wherein each clamp of the pair of clamps comprises a pair of opposing jaws movable between an open position and a closed position, wherein in the closed position, the pair of opposing jaws are configured to grip the test material, and wherein at least one of the opposing jaws includes a sawtooth surface configured to contact the test material and grip the test material when the opposing jaws are in the closed position.

10. The apparatus of claim 8, wherein the clamp module includes a tension sensor, the tension sensor being in communication with the pair of clamps and configured to determine tension of the test material once the test material is retained by the pair of clamps.

11. The apparatus of claim 1, wherein the tool module comprises:
    a holder configured to rigidly retain the electrosurgical tool, and
    a runner, the runner being coupled to a portion of the frame and configured to move in a single plane along a portion of the frame such that the tool module is movable in a single plane relative to the frame.

12. The apparatus of claim 11, wherein the tool module is configured to move in a plane perpendicular to a plane of motion of the carriage and the clamp module, wherein the motion of the tool module allows adjustment of a cutting depth of the electrosurgical tool relative to the test material.

13. The apparatus of claim 11, wherein the frame further comprises a vertical beam that extends perpendicular to the elongate rail, and the runner is coupled to the vertical beam and moveable along the vertical beam, and wherein the runner is coupled to an adjustment mechanism that is configured to allow incremental adjustment of the runner along the vertical beam.

14. The apparatus of claim 11, wherein the tool module further comprises an adjustable bearing coupling the holder to the vertical beam,
the adjustable bearing including an actuator configured to adjust an angular position of the adjustable bearing and holder relative to the vertical beam,
wherein the adjustable bearing is adjustable between a plurality of angular positions and the adjustable bearing allowing a user to adjust the angle of the electrosurgical tool within the holder.

15. The apparatus of claim 13, wherein the adjustment mechanism coupled to the runner is an electronic adjustment mechanism that is configured to move the runner relative to the frame, the electronic adjustment mechanism allowing predefined or incremental movement of the runner and the tool module relative to the frame.

16. The apparatus of claim 1, further comprising a high frequency power or current generator configured to be connected with the electrosurgical tool to provide a high frequency power or current signal to the electrosurgical tool to energize the electrosurgical tool.

17. The apparatus of claim 16, further comprising a controller and an actuator, the actuator being in electronic communication with the controller and the actuator being manually actuable between a first position and a second position, the controller being in electronic communication with the generator and configured to activate the generator and supply high frequency power or current signal to the electrosurgical tool when the actuator is in a first position, and deactivate the generator and stop supply of the high frequency power or current to the electrosurgical tool when the actuator is in a second position.

18. A method of testing the performance of an electrosurgical tool, the method comprising the steps of:
positioning a test material in a clamp module,
adjusting the clamp module to preload the test material to an initial preload,
adjusting an electrosurgical tool to an initial height and an initial angle,
activating power supply to the electrosurgical tool,
moving the electrosurgical tool or test material in one or more planes to create a cut in the test material, and
evaluating one or both of:
a cutting performance of the electrosurgical tool, based on one or more measurements taken as the electrosurgical tool performs the cut; and
a non-stickiness of the electrosurgical tool after the electrosurgical tool performs the cut.

19. The method of claim 18, wherein the step of adjusting the clamp comprises adjusting the clamp module to ensure the test material is under tension, and the step of moving the electrosurgical tool comprises moving the electrosurgical tool in a vertical plane relative to the test material to a cutting depth.

20. The method of claim 18, wherein the step of moving the electrosurgical tool or test material in one or more planes to create a cut in the test material comprises moving the clamp module in a horizontal plane for a predetermined distance such that the electrosurgical tool creates a cut in the test material.

21. The method of claim 18, wherein the step of evaluating the cutting performance comprises determining a resistance force versus a cutting depth of the electrosurgical tool for the cut, wherein the lower the resistance force the greater the cutting performance of the electrosurgical tool.

22. The method of claim 18, wherein the step of evaluating the non-stickiness of the electrosurgical tool includes:
measuring, using a digital weight balance, the final weight of the electrosurgical tool after the cut,
determining a weight gain based on the measured final weight and an initial weight of the electrosurgical tool before the cut, and
determining non stickiness based on the weight gain, wherein the smaller the weight gain the greater the non-stickiness of the electrosurgical tool.

* * * * *